(12) United States Patent
Litman et al.

(10) Patent No.: US 12,122,050 B2
(45) Date of Patent: Oct. 22, 2024

(54) METHOD AND SYSTEM FOR GENERATING A THERAPEUTIC MASSAGE PLAN

(71) Applicant: Aescape, Inc., New York, NY (US)

(72) Inventors: Eric A. Litman, Brooklyn, NY (US); David N. Walsh, Brooklyn, NY (US); Charles Paul Pace, Brooklyn, NY (US); Matthew Dicicco, Brooklyn, NY (US)

(73) Assignee: Aescape, Inc., New York, NY (US)

( * ) Notice: Subject to any disclaimer, the term of this patent is extended or adjusted under 35 U.S.C. 154(b) by 291 days.

(21) Appl. No.: 17/471,144

(22) Filed: Sep. 9, 2021

(65) Prior Publication Data

US 2022/0134551 A1 May 5, 2022

Related U.S. Application Data

(63) Continuation-in-part of application No. 17/319,062, filed on May 12, 2021, now Pat. No. 11,999,061, and a continuation-in-part of application No. 17/319,065, filed on May 12, 2021, now Pat. No. 11,998,289, and a continuation-in-part of application No. 17/319,064, filed on May 12, 2021, now Pat. No. 11,858,144.

(Continued)

(51) Int. Cl.
*B25J 9/16* (2006.01)
*B25J 9/10* (2006.01)

(52) U.S. Cl.
CPC ............ *B25J 9/1633* (2013.01); *B25J 9/106* (2013.01); *B25J 9/1664* (2013.01)

(58) Field of Classification Search
CPC ........ B25J 9/1633; B25J 9/106; B25J 9/1664; B25J 11/00; A61H 99/00; A61H 2201/1659; G16H 20/30; G16H 50/20; G16H 50/50

See application file for complete search history.

(56) References Cited

U.S. PATENT DOCUMENTS

| 5,876,325 A | 3/1999 | Mizuno |
|---|---|---|
| 6,494,851 B1 | 12/2002 | Becher |

(Continued)

FOREIGN PATENT DOCUMENTS

| CN | 203017580 U | 6/2013 |
|---|---|---|
| CN | 204684116 U | 10/2015 |

(Continued)

OTHER PUBLICATIONS

Peng et al, "Development of intelligent massage manipulator and reconstruction of massage process path using image processing technique," 2010 IEEE Conference on Robotics, Automation and Mechatronics, Singapore, 2010, pp. 551-556, doi: 10.1109/RAMECH.2010.5513135 (Year: 2010).*

(Continued)

*Primary Examiner* — Jaime Figueroa
(74) *Attorney, Agent, or Firm* — Van Pelt, Yi & James LLP (57) ABSTRACT

A system, method, and apparatus are provided for generating a dynamic, autonomous, machine-learning, and modifiable therapeutic massage plan. A system, method, and apparatus are provided for determining and executing the motion planning for directing one or more robotic arms to execute a sequence of motions while maintaining contact between their end effectors and a subject.

20 Claims, 4 Drawing Sheets

Related U.S. Application Data (60) Provisional application No. 63/076,366, filed on Sep. 9, 2020.

(56) References Cited

U.S. PATENT DOCUMENTS

| | | | |
|---|---|---|---|
| 6,585,668 | B2 | 7/2003 | Nissim |
| 6,607,499 | B1 | 8/2003 | Becher |
| D517,218 | S | 3/2006 | Kalen |
| D637,304 | S | 5/2011 | Feuerabend et al. |
| D637,305 | S | 5/2011 | Feuerabend et al. |
| D644,675 | S | 9/2011 | Abed |
| D665,093 | S | 8/2012 | Sedic |
| 10,034,813 | B1 | 7/2018 | Silver |
| 10,034,814 | B2 | 7/2018 | Zhang |
| D831,769 | S | 10/2018 | Tranchard |
| D833,028 | S | 11/2018 | Olivares et al. |
| 10,390,755 | B2 | 8/2019 | Goodall |
| D861,829 | S | 10/2019 | Wang |
| D867,609 | S | 11/2019 | Couto et al. |
| 11,197,799 | B2 | 12/2021 | Tian |
| 11,338,443 | B2 | 5/2022 | Eyssautier |
| 11,475,630 | B2 | 10/2022 | Tian |
| 11,529,900 | B2 | 12/2022 | Kim |
| 11,654,551 | B2 | 5/2023 | Huang |
| 2001/0014781 | A1 | 8/2001 | Nissim |
| 2002/0013641 | A1 | 1/2002 | Nourbakhsh et al. |
| 2005/0154295 | A1 | 7/2005 | Quistgaard |
| 2007/0000374 | A1 | 1/2007 | Clark et al. |
| 2007/0192910 | A1 | 8/2007 | Vu et al. |
| 2010/0261530 | A1 | 10/2010 | Thomas |
| 2011/0112549 | A1 | 5/2011 | Neubach |
| 2013/0198625 | A1* | 8/2013 | Anderson ............... G06F 3/016 715/701 |
| 2015/0298315 | A1* | 10/2015 | Shick .................. B25J 11/0005 704/260 |
| 2015/0351999 | A1 | 12/2015 | Brouse |
| 2016/0242995 | A1 | 8/2016 | Karkkainen |
| 2017/0079871 | A1 | 3/2017 | Zhang |
| 2017/0123487 | A1 | 5/2017 | Hazra |
| 2017/0156662 | A1 | 6/2017 | Goodall |
| 2017/0258598 | A1 | 9/2017 | Radermacher |
| 2017/0266077 | A1* | 9/2017 | Mackin .............. A61G 13/1235 |
| 2017/0281254 | A1 | 10/2017 | Bonutti |
| 2019/0000447 | A1 | 1/2019 | Shelton, IV |
| 2019/0160684 | A1 | 5/2019 | Gu |
| 2019/0167512 | A1 | 6/2019 | Forsythe |
| 2019/0201273 | A1* | 7/2019 | Soltani-Zarrin ....... B25J 9/0006 |
| 2019/0381271 | A1 | 12/2019 | Jo |
| 2020/0055195 | A1 | 2/2020 | Ignakov |
| 2020/0113636 | A1 | 4/2020 | Chino |
| 2020/0121556 | A1 | 4/2020 | Tian et al. |
| 2020/0126297 | A1 | 4/2020 | Tian |
| 2020/0206913 | A1 | 7/2020 | Kaehler |
| 2020/0281805 | A1 | 9/2020 | Qiu et al. |
| 2020/0391021 | A1 | 12/2020 | Sachs |
| 2021/0085558 | A1 | 3/2021 | Shin |
| 2021/0154852 | A1 | 5/2021 | Eyssautier et al. |
| 2021/0155136 | A1 | 5/2021 | Kim |
| 2022/0133589 | A1 | 5/2022 | Gruneberg |
| 2022/0134551 | A1 | 5/2022 | Litman |
| 2022/0387118 | A1 | 12/2022 | Litman et al. |
| 2022/0388165 | A1 | 12/2022 | Walsh et al. |
| 2022/0388168 | A1 | 12/2022 | Litman et al. |
| 2022/0414291 | A1 | 12/2022 | Eyssautier |

FOREIGN PATENT DOCUMENTS

| | | |
|---|---|---|
| CN | 206416184 U | 8/2017 |
| CN | 111053530 A | 4/2020 |
| CN | 113908035 A | 1/2022 |
| SG | 10201809094 A1 | 5/2020 |
| WO | WO-2021116554 A1 | 6/2021 |
| WO | WO-2021231663 A3 | 2/2022 |
| WO | WO-2022056181 A1 | 3/2022 |

OTHER PUBLICATIONS

Li et al; An Enhanced Robot Massage System in Smart Homes Using Force Sensing and a Dynamic Movement Primitive, 2020, Frontiers in Neurorobotics-Open Access, vol. 14: Article 30; doi: 10.3389/fnbot.2020.00030 (Year: 2020).*

Luo et al; "Tapping motion detection incorporate with impedance control of robotics tapotement massage on human tissue." 2018 IEEE 15th International Workshop on Advanced Motion Control (AMC) (2018): 160-165. (Year: 2018).*

Khoramshahi et al; Arm-hand motion-force coordination for physical interactions with non-flat surfaces using dynamical systems: Toward compliant robotic massage; 2020 IEEE, International Conference on Robotics and Automation (ICRA) May 31-Aug. 31, 2020. Paris, France, pp. 4724-4730 (Year: 2020).*

Luo et al; Robot Assisted Tapping Control for Therapeutical Percussive Massage Applications; 2017 IEEE International Conference on Robotics and Automation (ICRA) Singapore, May 29-Jun. 3, 2017, pp. 3606-3611 (Year: 2017).*

David, Pradeep, "Cobots—a helping hand to the healthcare industry," Nov. 24, 2017, Universal Robots, 6 pages.

International Search Report and Written Opinion for Application No. PCT/US2021/032111, mailed Jan. 24, 2022, 11 pages.

International Search Report and Written Opinion for Application No. PCT/US2021/049741, mailed Feb. 7, 2022, 5 pages.

Kraus, Rachel, "Bow down before this $310,000 massage megarobot, human: Who knew the robot uprising would be so good on the shoulders?," Health & Wellness Artificial Intelligence, Dec. 30, 2021, https://mashable.com/article/massage-robot-overlord, 4 pages.

Screen captures from YouTube video clip entitled "Robots can now give full-body personalized massages at home," 11 pages, uploaded Jul. 21, 2020, New Scientist, Retrieved from Internet: https://www.youtube.com/watch?v=t59TXsK1a6c.

Ulanoff, Lance, "Massage Robotics wants you to come and be touched by a robot—if that's your thing," Jan. 6, 2022, Techradar, The source for Tech Buying Advice, 13 pages.

Hu et al., "A massage robot based on Chinese massage therapy", 2013, Emerald Group Publishing, The Industrial Robot: an International Journal, vol. 40, No. 2, pp. 158-172. (Year: 2013).

Luo et al., "Human Body Trajectory Generation Using Point Cloud Data for Robotics Massage Applications", 2014 IEEE International Conference on Robotics & Automation (ICRA), Hong Kong Convention and Exhibition Center May 31-Jun. 7, 2014. Hong Kong, China, pp. 5612-5617 (Year: 2014).

Meera et al., "Path planning and motion control for a 3 DOF massaging robot," 2016 International Conference on Robotics and Automation for Humanitarian Applications (RAHA), Amritapuri, India, 2016, pp. 1-6, doi: 10.1109/RAHA.2016.7931883. (Year: 2016).

Minyong et al, "Expert massage motion control by multi-fingered robot hand," Proceedings 2003 IEEE/RSJ International Conference on Intelligent Robots and Systems (IROS 2003) (Cat. No. 03CH37453), Las Vegas, NV, USA, 2003, pp. 3035-3040 vol. 3, (Year: 2003).

Si et al., "Green Internet of Things Application of a Medical Massage Robot With System Interruption," IEEE Access, vol. 7, pp. 127066-127077, 2019, doi: 10.1109/ACCESS.2019.2939502. (Year: 2019).

Ex Parte Quayle Action for U.S. Appl. No. 29/732,265, mailed Dec. 2, 2022, 4 pages.

Massage instruments. (Design - © Questel) orbit.com. [Online PDF compilation of references selected by examiner] 17 pgs. Print Dates Range Feb. 24, 2004-Feb. 14, 2020 [Retrieved Nov. 18, 2022] https://www.orbit.com/export/LI CZAH96 B/pdf4/e9bd54bf-4351-4947- 8aae-2394fdea7fed-013045.pdf (Year: 2022).

* cited by examiner

METHOD AND SYSTEM FOR GENERATING A THERAPEUTIC MASSAGE PLAN

COPYRIGHT AND TRADEMARK NOTICE

Portions of the disclosure in this patent application contain material which is subject to copyright and/or trademark protection. The patent application owner has no objection to the facsimile reproduction of the published patent application or any resulting granted patent, as it appears in the U.S. Patent and Trademark Office records, but otherwise reserves all copyright and trademark rights whatsoever throughout the world.

CROSS-REFERENCE TO RELATED APPLICATION(S)

This application claims priority to U.S. Provisional Patent Application No. 63/076,366, filed Sep. 9, 2020, entitled "METHOD AND SYSTEM FOR GENERATING THERAPEUTIC MASSAGE PLAN," which is hereby incorporated in its entirety by reference hereto. This application claims priority to U.S. Provisional Patent Application No. 63/023,833, filed May 12, 2020, entitled "METHOD AND SYSTEM FOR AUTONOMOUS OBJECT MANIPULATION," and U.S. Non-Provisional patent application Ser. No. 17/319,062, entitled "METHOD AND SYSTEM FOR AUTONOMOUS OBJECT MANIPULATION," each of these applications being hereby incorporated in its entirety by reference hereto. This application claims priority to U.S. Provisional Patent Application No. 63/023,839, filed May 12, 2020, entitled "METHOD AND SYSTEM FOR AUTONOMOUS BODY INTERACTION," and U.S. Non-Provisional patent application Ser. No. 17/319,064, entitled "METHOD AND SYSTEM FOR AUTONOMOUS BODY INTERACTION," each of these applications being hereby incorporated in its entirety by reference hereto. This application claims priority to U.S. Provisional Patent Application No. 63/023,844, filed May 12, 2020, entitled "METHOD AND SYSTEM FOR AUTONOMOUS THERAPY," and U.S. Non-Provisional patent application Ser. No. 17/319,065, entitled "METHOD AND SYSTEM FOR AUTONOMOUS THERAPY," each of these applications being hereby incorporated in its entirety by reference hereto.

FIELD OF INVENTION

The present invention relates to a system, method, and apparatus for generating therapeutic massage plan. More specifically, the present invention relates to a system, method, and apparatus for determining and executing the motion planning for directing one or more robotic arms to execute a sequence of motions.

BACKGROUND

Robotics have been used for various applications, including assembly manufacturing and device testing. Such robotics have been used to test or manufacture textiles and devices. Other robotics have been used in medical surgery, requiring slow, precise movement. Often, the robotics are controlled in real-time, such as those robotics used in medical procedures, in order to control and monitor the actions of the robotics.

Some objects can be nonuniform in its characteristics, including texture, consistency and pressure points. For example, soft body objects, such as body tissue, may not be uniform in consistency and react to undue pressure differently than similar sized samples, due to the specific characteristics of the unique body tissue sample. Accordingly, available systems and methods for device testing or manufacturing are not configured to handle soft body objects, or their inherent inconsistencies. Likewise, real-time controlled systems and methods for medical procedures are not configured to handle soft body objects in an automated manner.

Accordingly, there exists a need for a therapeutic massage plan for the robotic handling of soft tissue, potentially nonuniform or nonhomogeneous, in a dynamic or automated system and method.

SUMMARY

Embodiments of the present invention provide a robotic control system changing the control system's contact point of the robot continuously based on sensed force. Embodiments of the present invention provide a robotic control system changing the controller gain selectively relative to the sensed orientation of the surface with which the robot is in contact.

Embodiments of the present invention provide for a massage generation system and method and apparatus comprising the motion planning for directing one or more robotic arms to execute a sequence of motions while maintaining contact between their end effectors and a subject. In an embodiment, the manipulation steps have additional specified tool patterns and geometric overlays, that are combined based on a tool criteria. These overlays typically are associated with variable pressures applied to a region of the subject's body. Different overlays will have increasing amounts of downward pressure, along with additional motion induced forces, and are designed to execute specific therapies at different depths of tissue.

Throughout this specification, "Massage Generation System" refers to a massage generation system and/or method and/or apparatus comprising the motion planning for directing one or more robotic arms to execute a sequence of motions while maintaining contact between their end effectors and a subject.

DETAILED DESCRIPTION

Figure 1:
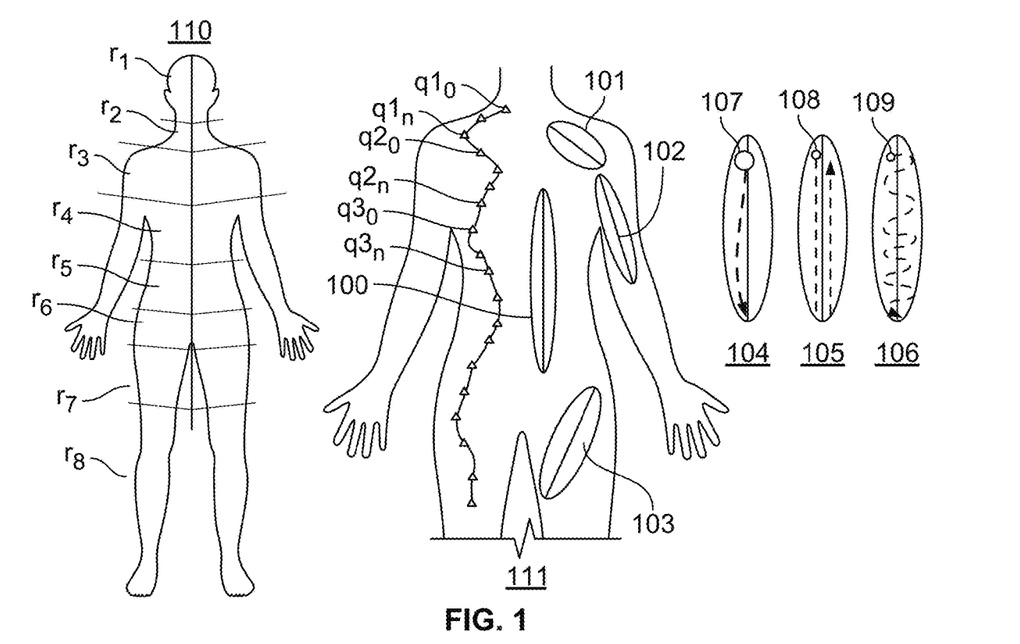
FIG. 1 shows an embodiment of a massage generation system according to the present invention.

Embodiments of the present invention provide for a massage generation system and method and apparatus which incorporates FIG. 1 of the above-claimed priority application METHOD AND SYSTEM FOR AUTONOMOUS OBJECT MANIPULATION, in which an embodiment of Massage Trajectory follows the Manipulation Trajectory. For example, the Applicator in the latter is similar to the Tool in the former. For example, the Subject in the latter can be similar to the Object in the former. For example, the Massage Table in the latter can be similar to the Worktable in the former. For example, the Massage Goals in the latter can be similar to the Manipulation Goals in the former.

Embodiments of the present invention provide for a Massage Generation System which generates a Massage comprised of Massage Strokes. The Massage Strokes are comprised of Manipulation Goals.

Embodiments of the present invention provide for a Massage Generation System which incorporates the Body Interaction System described in the priority METHOD AND SYSTEM FOR AUTONOMOUS BODY INTERACTION application, as identified above. For example, incorporating the priority application's FIG. 1 herein, the Applicator in the latter can be similar to the Touch Point in the former; the Subject in the latter can be similar to the Body in the former; the Support in the latter can be similar to the Table in the former; and, the Massage Goals in the latter can be similar to the Interaction Goals in the former.

Embodiments of the present invention provide for a Massage Generation System which incorporates the Tissue Treatment System described in the priority "METHOD AND SYSTEM FOR AUTONOMOUS THERAPY," application, as identified above. For example, incorporating the priority application's FIG. 1 herein, the Massage Applicator Contact in the latter can be similar to the Contact Point in the former; the Subject in the latter can be similar to the Viscera in the former; the Support in the latter can be similar to the Support in the former; and, the Massage Goals in the latter can be similar to the Treatment Goals in the former.

In an embodiment, the Contact Point is any point on the Applicator that is in contact with the Subject.

FIG. 1 depicts an embodiment of the Massage Generation System. The Subject (110) is depicted with a view of the back of the body. Regions $r_1$ to $r_8$ are depicted for the left side of the back of the body. Corresponding regions on the right side of the back of the body are shown as well. The detail of the Subject (111) depicts a Massage Plan on the left side of the back of the body, composed of Massage Strokes (q1, q2, q3). Between each Stroke is a short connection motion indicated as a dashed line which is automatically generated at runtime. Each Massage Stroke is composed of Massage Goals (e.g. $q1_0$ through $q1_n$).

In FIG. 1, within element 111, on the right side of the back of the body, several ellipses are depicted as elements 100 through 103. Each of these ellipses is bisected with a major axis depicted. The ellipses, for example, indicate regions of Target Muscles, including the Erector Spinae Group (100), the Trapezius Group (101), the Tricep (102), and the Gluteal Complex (103). The major axis indicates the alignment of the Muscle Fiber for the Target Muscle. The depicted Target Muscles are shown just for reference, their size, position, and other characteristics can target any muscle, any tissue type, and any region or combinations of regions.

In FIG. 1, generic Target Muscles are depicted in elements 104, 105, and 106. For Target Muscle 104, a Massage Pattern is depicted with a broken arrow (107), the path moves predominantly parallel to the Muscle Fiber of the Target Muscle depicted. This Massage Pattern is the Effleurage Massage Pattern, or simply Effleurage. For Target Muscle 105, a Massage Pattern is depicted with a broken arrow (108), the path moves predominantly parallel to the Muscle Fiber of the Target Muscle in motions that move up and down over the length of the depicted muscle. This Massage Pattern is the Stripping Massage Pattern, or simply Stripping. For Target Muscle 106, a Massage Pattern is depicted with a broken arrow (109), the path moves predominantly across the Target Muscle's Muscle Fiber. This Massage Pattern is the Cross-Fiber Massage Pattern.

Figure 2:
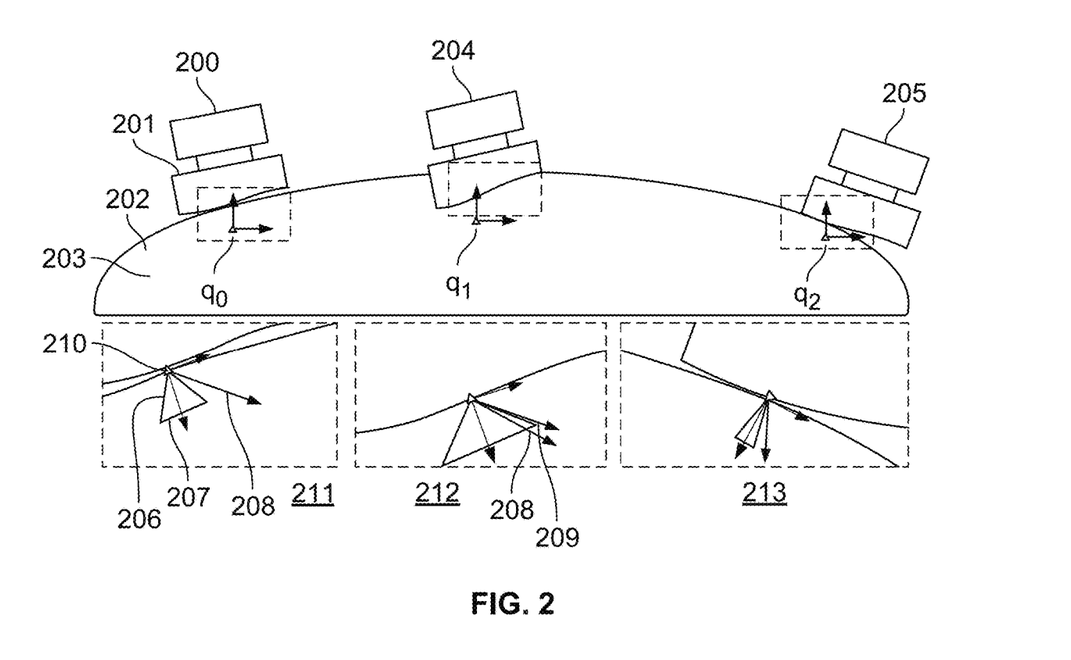
FIG. 2 shows an embodiment of a sequence of massage goals according to the present invention.

FIG. 2 depicts a sequence of Massage Goals (203), labeled here as q0, q1, and q2, relative to the Subject (202). For each Massage Goal, the Touchpoint (201) is in contact with the Subject at the Contact Point (210), resulting in a Contact Force (208). The component of the Normal Force is the component of the Contact Force that is parallel to the surface normal at the Contact Point. The surface properties of the Touchpoint and Subject materials that are in contact dictate the frictional force, which is represented as a Friction Cone (207). In the first Touchpoint position of the sequence, $q_0$ (200), the Contact Point (210) detailed in the insert at bottom left (211) illustrates a Contact Force that lies outside the Friction Cone (207) and the Touchpoint is free to slide across the Subject. At the second Touchpoint position of the sequence, $q_1$, detailed in the insert at bottom center (212), Contact Force is depicted (208) within the Friction Cone, indicating that the sliding motion of the Touchpoint will be halted. The Mitigation Strategy is used to change the Contact Force to a new value (209) such that motion can resume. The third Touchpoint position, $s_2$, detailed as an insert at the bottom right (213), depicts a new state where motion is not impeded.

The Controller progresses from one Manipulation Goal to the next Manipulation Goal in a Sequence. Various disturbances hinder the progress of the Touchpoint, including, but not limited to, friction and physical obstructions. The Controller utilizes a set of Mitigation Strategies to overcome the disturbances while maximizing the completion of the sequence of Manipulation Goals.

Embodiments of the present invention provides a system and method and apparatus for the execution of a wide range of therapeutic techniques from a single tool. The tool consists of a smoothly varying shape and hardness such that different points on the surface have different areas of contact and different surface properties. The different therapeutic techniques are achieved by varying the angle between the tool and the surface, varying the applied force magnitude, varying the angle of forces applied, and varying the addition of a motion overlay. Example overlays include applying linear motion along the muscle fibers, side-to-side motion across the muscle fibers, small circular motions in the plane of contact, and fast vertical oscillation motions into the contact plane. The contact plane is the plane tangent to the surface at the contact point of the tool. In one embodiment, the tool is similar to a Touchpoint. In a further embodiment, the therapeutic technique is similar to a Massage Type. In a further embodiment, the motion overlays are similar to Massage Overlays or Massage Patterns. In an embodiment, the applied force magnitude and the angle of the forces applied are similar to the Contact Force. In an embodiment, the areas of contact are similar to the Contact Point.

Embodiments of the present invention provides a system and method and apparatus to generate Motion Plans for one or more robotic arms which consist of a blended sequence of focused motion segments. Each segment is intended to encapsulate one or more intended therapeutic effects on one or more specific body targets, achieved through one or more dynamically selected virtual tools through a single end effector. The segments are generated by Recording Motion Capture. In a further embodiment, the segments are generated from dynamically generated motion paths. The Recording Motion Captures include motions, annotated data about what tool is attached and where contact is assumed to have occurred on the tool, and applied force magnitude and direction. Further, the Recording Motion Captures are recorded against a reference target while being applied by an operator or therapist. The motions in these Recording Motion Captures encapsulate specific intentions of the operator or therapist, which are annotated as metadata with the recording and persisted in a datastore. The Recording Motion Captures are recorded against Reference Subjects and transformed to a Neutral Template Subject, or Canonical Subject, for storage and subsequent transformation to a Target Subject when executing playback. Dynamically generated motion paths are created algorithmically given a set of input desired therapeutic effect, dynamic tool parameters, and target. Final motion plans are generated by concatenating the individual motion components, either pre-recorded or dynamically generated and inserting smooth blend motions in between each segment. The blend motions are not intended to have therapeutic effects and are implemented as spline motions along the surface of the reference body with either no downforce or minimal downforce to maintain contact with the surface. In an embodiment, the Motion Plans are similar to Massage Trajectories, the motion segments and motion paths are similar to Sequences or Massage Strokes, the blending is similar to Stroke Blending, the end effector is similar to a Touchpoint, the applied force magnitude and direction is similar to the Contact Force, the reference target and body are each similar to the Subject.

In embodiments, the robot augments the forces applied by an operator during the process of training massage strokes. The goal is to reduce the workload on the operator by not having to require the operator to generate as much of the force themselves. The system can measure the applied force, both into the body, which is the therapeutic load, and tangential to it, which is a frictional load, and augment them both separately to either increase the force applied to the body, which reduces the need for the user to apply this, or to overcome friction, again reducing the need for the operator to apply the load needed for this. The final applied load of the operator and the augmentation from the robot, is recorded as the final recorded stroke. When the augmented forces are added to the operator's force during the recording process, it is important to smoothly increase the applied augmentation load to produce a smooth final output force to be applied during playback.

In embodiments, the Subject Transformation includes the transformation of the recorded poses and forces relative to a body model representing the Subject at capture time, and the transformation from that body model to the body model of a Subject at playback time. A further embodiment stores the captured information transformed to a body model that represents a neutral Subject as an intermediate storage of the captured data. A further embodiment converts the positions and time between captured data positions to generate a velocity profile for the capture, allowing the playback to generate time goals for positions based on velocity to ensure that differences in Subject size do not degrade the intended playback pressures.

Figure 3:
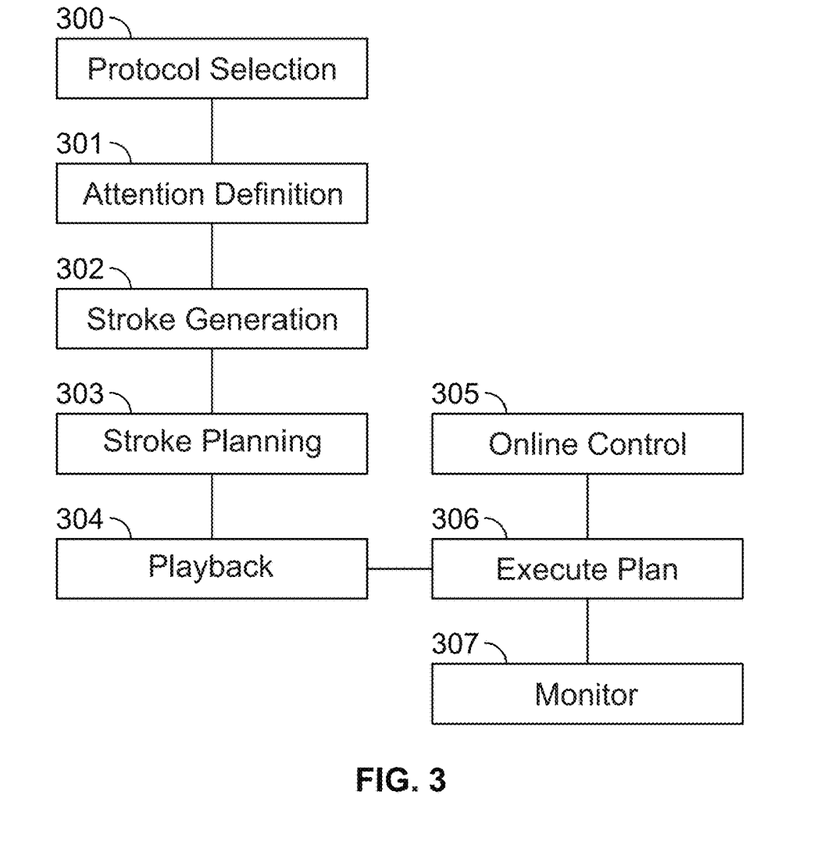
FIG. 3 shows an embodiment of a massage generation process according to the present invention.

FIG. 3 depicts the Massage Generation Process. The Protocol Selection (300) step determines which Massage Protocol will be designated for execution. The Attention Definition step (301) determines the amount of attention or avoidance that will be applied to the Massage. The Stroke Generation step (302) utilizes the Attention Definition and Massage Protocol to generate the Massage Strokes. The Stroke Planning (303) step assembles the Massage Strokes into a Massage Plan. The Playback step (304) generates the Tissue Treatment Goals from the Massage Strokes, adding them to the Massage Plan. The Execute Plan step (306) generates the Manipulation Commands for the robot from the Treatment Goals and Massage Strokes in the Massage Plan. The Online Control step (305) utilizes external system commands to provide control input to the Execute Plan step while it is executing the Manipulation Commands of the Massage Plan. The Monitoring step (307) monitors the Execute Plan step and the Online Control step to determine if a re-planning is required, if it is required, then the required change in planning is dispatched to any step from 300 through 304 and the Playback step integrates the new plan with the currently executing plan in coordination with the Execute Plan step.

In an embodiment, a Massage Protocol is defined as a temporal sequence of Stroke Specifications. The Stroke Specifications define the style, duration, intensity, and target for a treatment to be performed. The target is specified as a region of the body, potentially on the surface or a specific muscle. The Stroke Specifications are designed by a subject matter expert. The Stroke Specifications constitute a treatment plan containing a set of High Level Goals that include total duration, areas affected, and level of treatment.

In an embodiment, example High Level Goals for a specific Massage Protocol include: a thirty minute upper back relaxation massage, a sixty minute full body tension relief massage, and a thirty minute tennis workout recovery massage. In an embodiment, Massage Protocols are defined and provided to the user, the user subsequently selects a Massage Protocol from a provided list of available Massage Protocols in the Protocol Selection step (300).

In an embodiment of the Attention Definition step, the selected Massage Protocol is further refined with the addition of Attention Specifications for areas of more or less attention. Attention Specifications are defined through the Attention Definition step. In an embodiment, the user interacts with a touch screen interface to specify the Attention Specifications on a visual depiction of their body. The depiction includes specific areas or muscles on the body which the user wants either additional attention, less attention, or complete avoidance. The Stroke Specifications in the Massage Protocol are modified or removed based on the Attention Specifications. For areas of extra attention, the duration attribute of the specification is increased, for areas of less attention, the Stroke Specifications are either dropped from the protocol or the Stroke Specifications' duration and intensity attributes are decreased. Stroke Specifications are removed in areas designated in the Attention Specifications as areas to be avoided. In a further embodiment of the Execution Plan step, the Attention Definition and Attention Specification processing can be changed while executing the Massage Protocol.

In an embodiment, the Attention Definition step can occur while the Massage Protocol is executing, defining an Online Attention Definition. Further, the Online Attention Definition can incorporate input from the Subject undergoing manipulation or another user. The input can also include Trim Adjustments to spatially alter the massage trajectory, abort the execution of the massage, or indicate that more time should be spent at a specific location. In a further embodiment, the input includes dynamically adding region targets to the executing Massage Protocol.

In an embodiment, the Stroke Specifications are defined at the maximum intensity and any modification of the intensity is a decrease in the intensity. In the embodiment where the therapist records a stroke, the recorded stroke is defined as the maximum intensity of the stroke. In an embodiment where the user specifies higher intensity in a particular region, the intensity profile over the protocol can be used to alter the other stroke intensities to maintain the continuity of the strokes in the protocol to adhere to the protocol's intensity profile.

In an embodiment, the continuity of strokes when adjusting to user preferences is achieved by beginning with Massage Protocols which incorporate the maximum level of intensity required at any given region of the massage and only removing strokes as the Stroke Specifications do not match with the user provided preferences. This means that a full, maximum intensity stroke plan is designed by the therapist which is scaled back as appropriate. This is performed to avoid the problem of not knowing where, within the timeline of strokes, a new stroke would be inserted if the user designates a desire for additional strokes at a high intensity on a particular region. There is a desire to maintain a continuity of increasing and decreasing intensity within a particular region of the body and then a contiguous flow of working regions across the body within a Protocol, so an arbitrary stroke would be difficult to insert after the fact, without expert knowledge.

In an embodiment, one of the Stroke Specifications which can be selected by the designer of the Massage Protocol is the treatment of problem areas (called Adhesions or Trigger Points) through the direct application of focused pressure on the problem area. These areas are not known beforehand and are detected through palpation by the massage therapist. For trained therapists, this palpation can occur during strokes that are applying their own therapeutic effect. In the Massage Generation system, this application of focused pressure strokes will require knowledge of the target goals which are calculated while the massage is being performed. The Stroke Specification for this type of treatment within the Massage Protocol will simply allocate a maximum duration of allotted time for treatment. At execution time, the locations of problem areas will be automatically detected by a palpation system and will be stored for use during this specific Stroke Specification. If no problem areas are found, this stroke can be skipped, if a small number is found, the duration can be shorted, or if a large number of problem areas are found this duration can be filled with as many treatment strokes as are possible or it can be expanded, as designated by the user via the user interface touch screen. The focused pressures include the application of variable pressure.

The ability to partition recorded/generated sequential segments and then subsequently recombine them is critical to differentiating the present invention. This enables a wider variety of massages to be generated for each protocol. Objectives include effectively blending the sequences, ensuring Spatial Continuity, achieving Treatment Goals, smooth transitions, coordinated movement, producing a pleasurable experience. Rearranging the order and repetition of sequences based on personal preferences. Rearranging operations including repeat, skip, pause, resume, and user spatial control (jogging).

In an embodiment, the Strokes are generated through a Procedural Stroke Generation process. The Stroke Database is utilized to generate a Procedural Stroke. The Procedural Stroke is a parameterization and a function that generates a Stroke that sequentially follows from the one or more preceding Strokes. The generation of the parameters for the Procedural Stroke are derived from both the metadata and trajectory information of the preceding Strokes.

In an embodiment, the Procedural Stroke Generation process includes several layers of targeted goals: High Level Procedural Goals, Medium Level Procedural Goals, and Low Level Procedural Goals. The High Level Procedural Goals include targeting muscles, regions, intensity levels, and customized treatment goals. The Medium Level Procedural Goals include muscle definition, orientation of muscles, motion and force goals, and percussive overlays. The Low Level Procedural Goals include Motion Generation Goals, both Offline Motion Generation and OnlineMotion Generation Goals that achieve kinetic goals such as a minimum and maximum position variance, a minimum and maximum velocity, a minimum and maximum acceleration, and a maximum jerk.

In an embodiment, the Percussive Overlays are defined utilizing Pressure Goals that are focused on producing variations in pressure.

Figure 4:
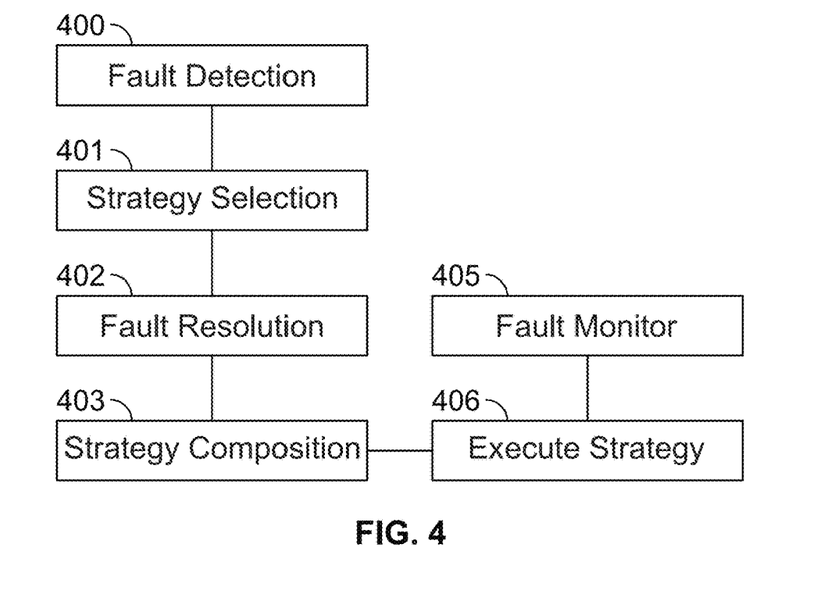
FIG. 4 shows an embodiment of a fault mitigation process according to the present invention.

FIG. 4 depicts an embodiment of the Fault Mitigation Process. The Fault Detection step (400) detects when a Progression Fault has occurred while executing the Massage. The Strategy Selection step (401) selects one or more Mitigation Strategies for the Progression Fault. The Fault Resolution step (402) defines the Resolution Strategy for the selected Mitigation Strategies. The Strategy Composition step (403) combines the Mitigation Strategies into a Composite Mitigation Strategy. The Execute Strategy step (406) executes the Composite Mitigation Strategy. The Fault Monitoring step (405) monitors the execution of the Composite Mitigation Strategy and determines if the Fault has resolved or whether the fault has changed to the point where the process should return to the Fault Detection step.

In an embodiment, the Fault Detection Step identifies the lack of progress in the execution of the massage. It does this by monitoring the Cartesian position tracking error. When the error passes a threshold, an event is generated in the Progress State Management. These thresholds can be adjusted with respect to commanded velocity, as tracking can be difficult to maintain at higher speeds. In an embodiment, the threshold is determined by a scaling factor of the tracking error relative to the down force, where the larger the down force, the larger the threshold on the tracking error.

In an embodiment, the Strategy Selection Step determines the strategy to apply for the detected fault. The strategies include decreasing or changing the magnitude or direction of the force applied. In cases where the strategies reach their maximum mitigation state and the fault is still occurring, additional strategies are selected. In an embodiment, the additional strategies include slowing or stopping the position goals, modifying the position goals to lift the arm off the surface, or completely aborting the massage.

In an embodiment, the Fault Resolution Step determines when to resume normal unmitigated operation when in a fault state. When the tracking error has dropped below a predetermined threshold for a predetermined amount of time, the fault is considered resolved and the state is reverted to a nominal state. In an embodiment, the threshold that triggers the fault state and the threshold that reverts the system back into a nominal state aren't the same threshold.

In an embodiment, the Mitigation Strategies include Force Reduction, Friction Compensation, Force Redirection, and Online Motion Generation.

In an embodiment, the Force Reduction scales the entire feedforward force vector's magnitude. The scaling continues through the entire mitigation process. In a further embodiment, the Force Goal itself is scaled before the Massage Plan is executed.

In an embodiment, the Friction Compensation factors the measured forces into the orthogonal components that are parallel to the surface normal and tangent to the surface normal. The tangential component is considered to be the component of the force corresponding to cancel friction. The mitigation strategy compensates for additional friction by increasing the tangential component when the measured force tangentially is high.

In an embodiment, the Force Redirection assumes that the progress of the massage is being impeded by a physical obstacle. The orientation of the Touch Point is altered to follow the contour of the obstacle. Orientation Variance Limits are defined to limit the degradation of the massage.

In an embodiment, the Online Motion Generation manages the higher order dynamics of the massage. Desired goals are filtered using the measured position changes of the arm. The filtering limits the arm's velocity, acceleration, and jerk to predefined thresholds.

Figure 5:
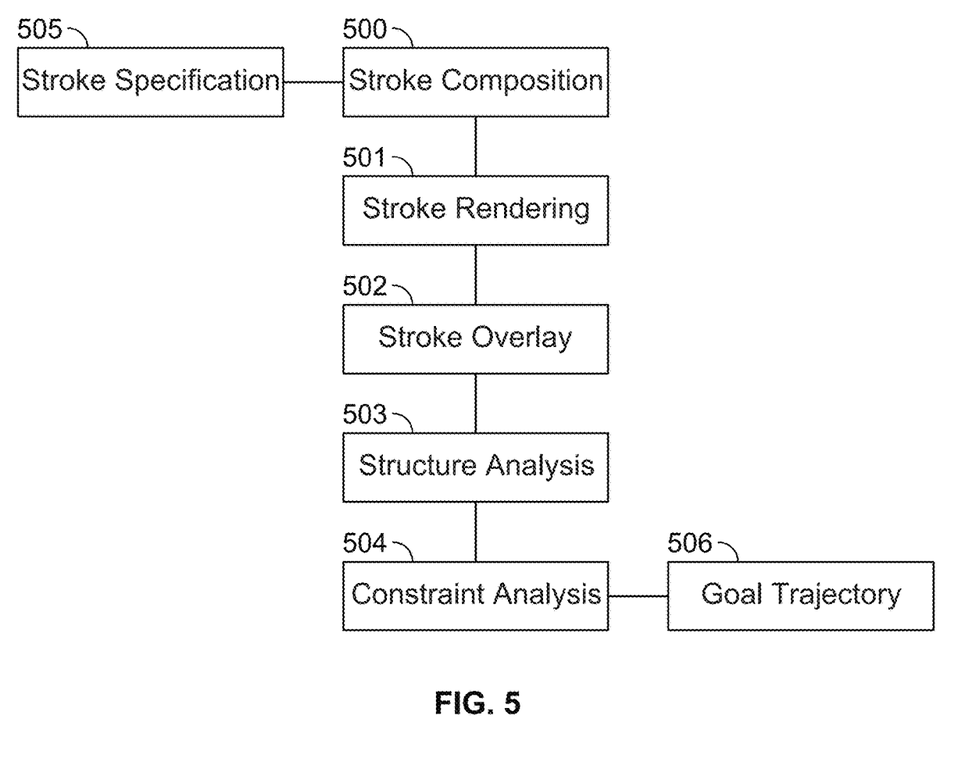
FIG. 5 shows an embodiment of a stroke generation process according to the present invention.

FIG. 5 depicts an embodiment of the Stroke Generation Process. The Stroke Composition step (500) takes a Stroke Specification (505) as input and utilizes a Stroke Database and a Stroke Request to generate a detailed Stroke Specification input step. The Stroke Rendering step (501) transforms the Stroke Specification into a Rendered Stroke that adheres to the Target Requirements. The Stroke Overlay step (502) adds additional motion overlays targeting certain manipulation of tissue. The Structure Analysis step (503) conforms the stroke to the tissue structure. The Constraint Analysis step (504) constrains the stroke to achievable goals. The output is a set of goals (506) from the Goal Trajectory output step. In an embodiment, the Stroke Generation Process is used by the Stroke Generation step (302).

In an embodiment, the Stroke Composition Step receives the Muscle Target as input along with the desired Massage Style, User Preferences, Targeted Tissue Layer, and Treatment Points. Treatment Points are any of the following: Adhesion, Trigger Point, Knot, Tension, Soreness, Tingling Sensation, Numbness, and any other identifiable point on the body.

In an embodiment, the Generator matches the last stroke's characteristics to the Selector's result set of strokes, the matching criteria is based on kinematic considerations coming from the end portion of the previous stroke. These considerations include: the position of the end of the stroke, the linear and angular velocity at the end of the stroke, the radius of curvature of a spline fit to the end of the stroke, the exit direction defined by a tangent vector at the end of the stroke, and the acceleration and jerk properties of the end of the stroke.

In an embodiment, the Selector uses Query Criteria to generate a list of Strokes. The Query Criteria includes Metadata Tags that include location, target, duration, and intensity. Additional Metadata Tags include the target, which includes the muscle target, a group of muscles to target (e.g. upper back, lower back). Additional Metadata Tags include the Intensity, which is a subjectively determined attribute of the massage.

In an embodiment, the Synthetic Generator utilizes Metadata Tags as Query Criteria to identify Matching Strokes. In an embodiment, one of the Strokes in the Matching Strokes is selected as the Matching Stroke. In an embodiment, the Matching Strokes are utilized as feature data to fit a Stroke Motion Model, a model of the motion and force generating functions. In an embodiment, the Metadata Tags are combined with the Stroke Motion Model to generate new strokes. The Stroke Motion Model includes motion and force characteristics.

In an embodiment, the Stroke Rendering Step utilizes a specified Massage Style, generating generic motion primitives that are applied to the Massage Region of the muscle. The Stroke rendering is based on the muscle attachment points. The Stroke Rendering generates long straight motions parallel to the muscle fiber, running to/from the muscle attachment points. The Stroke Rendering utilizes the Target Tissue Layer specification to generate motions specific to the Treatment Points.

In an embodiment the Stroke Overlay Step utilizes a Massage Style specification, generating motion overlays that are added to the generic motion, to generate the desired therapeutic effect. These overlays consist of both force goals to achieve a desired downward pressure into the tissue and motion overlays to add motion changes like crossfiber motions or circular friction. Frictional forces are added to the force goals based on the desired motion direction, the downforce, and a friction model. The downward pressures include the application of variable pressure.

In an embodiment, the Structure Analysis Step generates a set of modifications to the Massage Goals, modifying the goals based on underlying tissue structures. For example, when pushing up against the side of a muscle inline with the muscle fiber. For this example the initial motion would be along the side of the muscle, a downforce and friction force would be applied to achieve the desired therapeutic effect and then the downforce would be angled inward, towards the longitudinal axis of the muscle to produce a desired contour following profile.

In an embodiment, the Constraint Analysis Step reviews the Massage Goals to identify goals that don't meet a Feasibility Criteria. An example of a Feasibility Criteria includes the case when there motion would result in velocity or accelerations that exceed minimal safety thresholds. Also, Feasibility Criteria include the absolute and relative changes in force that would exceed safety thresholds.

In an embodiment, the Stroke Generation Process accounts for friction and performs progression management when utilizing strokes generated from natural recordings. When these natural recordings are generated, the integrated force/torque sensor used to measure the downforce used to apply tissue treatment additionally measures the side loads generated by friction as the touchpoint slides across the body. By taking these measured reaction forces as the setpoints for the desired force to apply during execution of the recorded stroke, the system provides additional forces to overcome the friction measured during recording. Assuring that as the surface properties generate friction at playback time similar to those produced at recording time, the friction can be sufficiently compensated. Small deviations in friction properties are handled as a disturbance to the controller. Substantial changes in friction properties trigger the online progression management system, as described.

In an embodiment, the motion plans discussed above are extended in a further embodiment by allowing for a plan to be modified at any point in its execution such that some portion of the plan, occurring at a time subsequent to the replan event, may be modified from its original intent. This is achieved by replacing entire motion segments with new ones that have a different intended therapeutic effect or by modifying a global parameter of the plan, such as maximum allowable applied force or a shape parameter on the transformation used to map the motion trajectory to the current subject. In an embodiment where complete motion segments are swapped with alternative motion segments, either type of segment, pre-recorded or dynamically generated, are replaced with segments of the same or opposite type.

In an embodiment, the Massage Definition Process starts with the selection of predefined Massage Strokes that are Composited together into a Massage Plan and then Adapted to the Subject. Strokes can be generated through a Natural Stroke Generation Process or a Synthetic Stroke Generation Process. The Massage is Adapted to the active tool based on the Tool Definition.

In an embodiment, the Composition of Strokes form a Massage Plan by concatenating individual Massage Goals from one Massage Stroke after the Massage Goals from another Massage Stoke, in a time dependent sequence, while adding artificially generated interpolation Massage Goals between the current Massage Goals. In an embodiment further, Interpolation of Massage Goals includes generation of a smooth linear motion in space from the end of the first Massage Stroke along the surface of the Subject with force goals decreasing their magnitude to zero, a translation along the surface of the Subject, and then a smooth linear transition motion with an accompanying increasing of the force magnitude to the first Massage Goal of the next stroke.

In an embodiment, the Trajectory Mitigation Strategy utilizes tracking and fitting of the Subject's Body to maintain the accuracy of the Massage Goals. In an embodiment, the Body Fitting process is performed continuously and the Trajectory Retargeting is also performed continuously to handle both tracking and fitting of the Massage goals.

In a further embodiment, the Trajectory Mitigation Strategy tracking is achieved through tracking discriminant features on the Subject's Body to determine the displacement of the body, and it's constituent surface positions, relative to the initial Body Fitting. The fitting is achieved through interpolation of the Massage Goals in Cartesian space based on the displacement from tracking. In an embodiment, the interpolation is linear interpolation of the 3D Massage Goal positions and SLERP interpolation of the Massage Goal orientations. Similarly, the other associated goals are likewise interpolated. In a further embodiment, the transformation of the Massage Goals is achieved through fitting a Spline to the goals and transforming the Massage Goals associated with their mapped position on the Spline to the position of those Spline points in the transformed Spline, which is transformed by the displacements. In a further embodiment, the tracking is enhanced using an Extended Kalman Filter to allow the discriminant features to be tracked when not visible based on their relationship to other discriminant features.

In another embodiment, the linear interpolation is replaced by a higher order polynomial interpolation. In a further embodiment, the linear interpolation is replaced by a piecewise linear or a piecewise polynomial modeled by a Spline.

In an embodiment, the Massage Motion Planning Process starts with Tool Definition and Subject Identification. The Tool Definition includes the geometry and material properties of the Tool. Subject Identification includes identifying the body shape of the subject, pose of all the joints of the Subjects, gross position of the center of the Subject's body with respect to the table, and an estimate of the internal structures of the Subject. Body shape, pose, and position are calculated from data generated by an imaging system mounted above, around, or in any proximity to the subject consisting of one or more depth sensing cameras. In an embodiment, the internal structures of the body are estimated by modeling how the body structures vary with body shape.

In an embodiment, the Trajectory Mitigation Strategy, based on tracked motion, articulation, and shape variation or the Subject's Body, adds or removes Massage Goals from a Massage Stroke, in a time dependent sequence, while removing Massage Goals or adding artificially generated interpolation Massage Goals between the current Massage Goals. In a further embodiment, this Trajectory Mitigation Strategy is only performed when the tracked motion, articulation, and shape variation or the Subject's Body changes more than a predefined threshold.

In an embodiment, the Configuration Space of robot poses is primarily constrained by the mounting position of the one or more arms relative to the position of the Subject's Body. Secondarily, the Configuration Space is constrained by the size, shape, and pose of the Subject's Body and limbs. Another Configuration Space constraint is the operation of the robot arm on extreme objects, when a body is extremely small or large it has an effect on the arm configuration and operation. Configuration of the robot when operating different tools has operational constraints. In an embodiment, the constraints of the Configuration Space are used to alter the stroke to not exceed the operating capabilities of the robot. In an embodiment, the alteration of the stroke is the deletion of the violating segment followed by an Interpolation of Massage Goals as mentioned in the Composition definition.

In an embodiment, a Trajectory Mitigation Strategy is utilized when the Trajectory Retargeting of a planned path is not topologically valid or imposes an operational constraint on the robot. In a further embodiment, the Trajectory Mitigation Strategy is utilized when the robot is constrained by the pressure goals combined with configuration poses near or outside the operating capabilities of the robot. In a further embodiment, the Trajectory Mitigation Strategy is utilized when the robot goals of position and force create a condition where progress along the trajectory is stalled. In an embodiment, the Trajectory Mitigation Strategy is defined as a modification of the goals to reduce friction and resume progress along the trajectory. These adjustments temporarily reduce the effectiveness and/or accuracy of the replayed trajectory but are applied to provide a method for completing the trajectory. Additional friction is expected in situations where the surface of the Subject does not match the model, either in stiffness or in friction coefficient or other unknown or unmodeled effects.

In an embodiment, each of the Interaction Goals contain a desired arm pose that the robot will achieve as a secondary goal while targeting the primary position goal and/or force goal. This secondary goal is achieved by moving the arm through its null space, defined as the redundant postures that can be used to achieve an end effector, or tool contact point, position and orientation. These goals are specified as a Posture Goal and consist of joint goals for all arm joints. Posture goals are computed as part of the overall trajectory and modified at runtime based on the current position of the Interaction Goal with respect to the base of the robot.

In an embodiment, the Posture Goals are adjusted to increase the manipulability of the robot. In an embodiment, the Posture Goals are adjusted to reduce the auditory noise generated by the robotic arm motors.

In an embodiment, the Posture Goals are adjusted to reduce the joint velocities or accelerations of the robotic arm links to keep them under a predetermined threshold.

In an embodiment, the Posture Goals are adjusted to reduce the torque loading on specific joints. In a further embodiment, the reduction in torque loading is targeted specifically to the first inboard joint who's motor axis is positioned orthogonally to the contact frame's force normal. In a further embodiment, the reduction strategy adjusts the torque evenly across the joints based on the current manipulability of the robotic arm.

In an embodiment, the Posture goals are adjusted to reduce the required torque commands to the joints, such that each joint remains below a specified torque limit. In a further embodiment, the torque limits correspond to a manufacturer specified limit. In a further embodiment, the torque limits correspond to an empirically derived mechanical limit.

In an embodiment, there are Operating Strategies for the motion planning used to generate the Massage Plan, including specification of the traversal of grids, cells, and regions of the Subject. In an embodiment, the present invention provides full coverage of the Subject's back by allocating time to every region and ensuring coverage within the regions through cell based grid traversal.

In a further embodiment, the Massage Plan is considered complete when the Touchpoint has traversed the entirety of the Subject's body that is within the reach of the robot. In an embodiment, the system incorporates tissue assessment and repeats treatment on regions of the Subject until high level goals of tissue treatment are achieved. In an embodiment, touch based sensation is actuated by the Touchpoint to assess the state of tissue which is then fed back to the coverage planner to perform re-treatment of areas already covered in an initial massage motion.

In an embodiment, the Operating Strategies focus on geometric constraints, following contours on decision surfaces and avoiding Anatomical Obstacles and Virtual Obstacles. In an embodiment, the decision surfaces are spatial topological surfaces, including: the surface of the Subject, the surface of internal tissue such as muscle, adipose, tendon, and bone. The Anatomical Obstacles are specific pressures over adipose tissue that can trigger tickling resposes, tissue near boney surface prominences, and the edge of moving muscle layers over bone layers such as in the scapular region. Virtual Obstacles include sensitive regions, separation zones for robotic arms, and protection volumes for Operators and Therapists in close proximity to the Subject.

In an embodiment, the Operating Strategies include Anatomical Rewards, Physiological Rewards, and Virtual Rewards. Anatomical Rewards include reducing tissue stiffness, Adhesion reduction, Referred Pain Region reduction, Trigger Point stiffness release, Range of Motion increase. Physiological Rewards include Blood Flow increase, Blood Oxygenation increase, Respiration Rate decrease, EEG targets, HRV decrease. Virtual Rewards include Contact Surface Area minimized or maximized, Tool and Robotic Arm clearance from Subject maximized. In an embodiment, Virtual Rewards include minimizing joint rotational velocity, minimizing joint torque, and minimizing robot motor noise. In a further embodiment, goals can include the desired pressure requiring a specific area of the touchpoint and a specific force to be applied. In a further embodiment, a goal includes maximizing manipulability of the robotic arm. The desired pressure includes the application of variable pressure.

In an embodiment, the Subject's Body State is determined through the assessment of the Subject's participation in activities. In a further embodiment, the activities for Body State assessment include sitting incorrectly at a desk, pitching a ball, and swinging a golf club. For each activity, the Body State is associated with Implicated Tissue adversely being affected by the activity, the Implicated Tissue is targeted with customized Massage Strokes.

In an embodiment, the Subject's Body State is determined through the assessment of the Subject determining a known medical condition. In a further embodiment, the medical condition includes corollary conditions, diabetic conditions, and chronic myofascial pain. For each condition, Implicated Tissue adversely affected by the condition is targeted with customized Massage Strokes.

In an embodiment, the Subject's Body State is determined through the assessment of the Subject indicating regions where they are experiencing pain. For each indicated region, implicated tissue associated with the pain is targeted with customized Massage Strokes. In a further embodiment, the implicated tissue is located near the painful region. In a further embodiment, the pain is referred, Implicated Tissue at a remote region as the source of the pain and Massage Strokes are generated to target these regions of referred pain.

In an embodiment, the Subject's Body State is determined through the assessment of the Subject indicating regions where they are experiencing tension. For each indicated region, implicated tissue associated with the tension is targeted with customized Massage Strokes. In a further embodiment, the Implicated Tissue is located near the tense region. In a further embodiment, the tension is referred, implicating tissue at a remote region as the source of the tension and Massage Strokes are generated to target these regions of referred tension.

In an embodiment, the pain and tension described above is associated with Adhesions or Tissue Adhesions.

In an embodiment, Massage Stroke and Massage Protocols are defined by Body Script, a human-readable script language or text code. In an embodiment, Body Script defines specifications for Massage Types, Massage Overlays, Treatment Targets, and any parameter of the Massage Generation Process and any parameter in the Massage Plan.

In an embodiment, the Body Script code is compiled into Geometric Primitives that are stored. The Geometric Primitives are utilized to generate Massage Goals when generating a Massage Plan.

In an embodiment, Geometric Primitives are generated based on Geometric Parameters. The generated Geometric Primitives further generate patterns of pose goals and force goals. These patterns are subsequently ordered, blended, and layered to generate the Massage Plan. In an embodiment, the Geometric Parameters include start pose, end pose, velocity, desired downforce, and path descriptors required to render the path of the generated goals.

In an embodiment, the BodyScript Compositing System is similar to a nonlinear video editing system. Similar to how the video editing system allows the user to select video content from a library of video clips, the Compositing System allows the user to select Stroke content from a library of Strokes. Similar to how the video editing system allows the user to place the video clips in sequence and then transitions are inserted between clips and after effects can be applied on top of the output stream, the Compositing System allows the user to place the Strokes in a sequential order, insert transitions between the Strokes, and add effects over the Strokes. In an embodiment, Strokes are sets of one or more Geometric Primitives.

In an embodiment, the Subject interacts with the Massage Generation System, giving input to the system in the form of points or paths indicated on a depiction of their body. The system utilizes this input to guide the Massage Generation System to enter into a Jogging Mode of operation. The Jogging Mode has several Jogging Interaction Styles that vary how the Subject's interactions are interpreted for Massage Generation.

In an embodiment, there is a Jogging Interaction Style that directly interprets the Subject's interaction in terms of position and pressure as the exact position on the body with a goal pressure proportionally matching the Subject's interaction pressure. The goal pressures include the application of variable pressure in addition to the Subject's interaction pressure.

In an embodiment, there is a Jogging Interaction Style that indirectly interprets the Subject's interaction in terms of position and pressure by matching existing Massage Strokes with characteristics similar to the interaction pattern. Additional pressure variability patterns are optionally added to the pressure associated with the interaction pattern pressure.

In an embodiment, the Subject interacts with the Massage Generation System during execution of a Massage Plan. The interaction is in the form of indicating Subject Sentiment on a Graduated Scale. The system performs Sentiment Adaptation based on one or more Sentiment Samples.

In an embodiment, the Sentiment Adaptation triggers the Massage Generation System to alter the Massage Plan by replacing Strokes with a negative Sentiment occurring later in the Massage Plan with a repeat of Strokes with positive Sentiment.

In an embodiment, the Massage Planning Process is preceded by a Pressure Calibration Process. The Pressure Calibration Process performs a series of interactive samples on the Subject and the Subject interacts with the Massage Generation System to indicate the Subjective Pressure Sensation perceived by the Subject.

In an embodiment, the Subjective Pressure Sensation is performed when the massage is trained in order to establish a Training Subjective Pressure Sensation measure. This measure is normalized relative to the Absolute Pressure Measurement that the Massage Generation System utilizes to estimate the pressure being applied to the Subject, resulting in the Canonical Subjective Pressure Sensation.

In an embodiment, the Subjective Pressure Sensation of a Subject is compared to the Canonical Subjective Pressure Sensation to determine the Pressure Transform for the Massage Plan. The Pressure Transform alters the Massage Plan to (1) increase or decrease Massage Pressure for the whole massage, (2) increase or decrease the Massage Pressure for particular regions of the body, (3) increase or decrease the Massage Pressure based on underlying tissue constituency, including predominance of bone, fat, or muscle.

In an embodiment, the Pressure Calibration is performed on the same Subject at set intervals to determine changes in perceived pressure. Pressure is applied to different regions of the body while the user inputs a quantitative assessment of the pressure, giving both an overall sensitivity and a regional sensitivity/tolerance. This is used as a Pressure Bias for robot operation. In an embodiment, the Pressure Bias scales the pressure based on the Pressure Bias divergence from a baseline measurement performed during another massage session. The other massage sessions can include the session in which the massage was originally recorded, other sessions in which a single Subject was massaged, and/or other sessions for different Subjects.

In an embodiment, the Pressure Calibration pressures are optionally accompanied by the application of variable pressure.

In an embodiment, an Operating Strategy is defined to apply a progression of tissue layer manipulation or Treatment Goals. These Treatment Goals have a specific sequence defined. In an embodiment, the sequence is determined by matching "treatment" profiles through a compatibility criteria.

In the priority-claimed "METHOD AND SYSTEM FOR AUTONOMOUS OBJECT MANIPULATION" application, an embodiment describing the Controller, a Robot control, is formulated to incorporate feedback error in the Object Space. The input to the Controller is calculated with positions laid out on a 2D plane which is then mapped to the surface of the 3D body. This mapping is done with existing texture mapping techniques but is extended to include heights above or below the surface. The Controller allows object deformation without losing surface positioning as the 2D mapped points would stay mapped to the surface even as it is deformed. A further embodiment utilizes a 2D path drawn on a rendering of the body to act as the 2D mapped points. One or more of these embodiments are incorporated herein in combination with and without the embodiments of the present invention described herein.

In an embodiment, Effleurage Pattern is a Tool Manipulation Pattern composed of light sweeping motions with light pressure, targeting reflexive muscle relaxation, increased blood flow, and warming up of muscle tissue.

In an embodiment, the Stripping Pattern is a Tool Manipulation Pattern oriented relative to the targeted muscle's dominant fiber direction. The Pattern favors motion in line with the Dominant Muscle Fiber. The Therapeutic Goal is elongation of the muscle. The applied pressure is generally greater than that applied by the Effleurage Pattern as the target tissue tends to be deeper in the Body.

In an embodiment, the Cross-fiber Pattern is a Tool Manipulation Pattern oriented relative to the targeted muscle's dominant fiber direction. The Pattern favors motion across with the Dominant Muscle Fiber. The Therapeutic Goal is separation and excitement of the muscle fibers. The applied pressure tends to be greater than that applied by the Effleurage Pattern and generally greater than that applied by the Stripping Pattern as the target tissue tends to be deeper into the body and due to the increased resistance of moving across the muscle fibers rather than along them. In a further embodiment, the Therapeutic Goal is the loosening of Adhesions.

In an embodiment, the Ischemic Compression Pattern is a Tool Manipulation Pattern where a large downward force is applied to a specific, static target on a muscle or group of muscles. The Therapeutic Goal is the localized blockage of blood flow to the target for a duration of time and the resurgence of that blood flow upon release of the pressure. This Pattern can be applied to trigger points as part of their treatment, or at lower pressure to generic muscle groups for relaxation.

In an embodiment, the Tapotement Pattern is a Tool Manipulation Pattern that utilizes rhythmic percussion of the Touchpoint. In an embodiment, there are five variations of the Tapotement Pattern including Beating, Slapping, Hacking, Tapping, and Cupping. The Beating variation applies repeated striking of the surface of the Subject's Body while raising the Touchpoint above the surface of the Body and bringing the Touchpoint in rapid contact with the body while "bouncing" the Touchpoint when the desired pressure is achieved. The Slapping variation applies an angular swinging of the Touchpoint to bring the surface of the Touchpoint in contact with the Subject's Body at a slight angle until the desired pressure is achieved. The Hacking variation is similar to the Beating variation utilizing a narrower "bladed" surface area of the Touchpoint. The Tapping variation is similar to the Slapping variation where the surface area of the Touchpoint in contact is minimized. The Cupping variation is similar to the Slapping variation with a focus on using a larger surface area with a lighter contact. The therapeutic goal of these Tapotement Patterns is to stimulate the Subject's Body, often in preparation for deeper manipulation.

In an embodiment, for any of the Tool Manipulation Patterns, a variable pressure pattern is optionally applied to achieve the desired therapeutic effect.

In an embodiment, Sequencing and Stitching trajectory segments includes the stitching of position goals, force goals, and contact reference frame goals. Where the Massage Goals overlap spatially, there is an interpolation of the goals, sequencing of the different goals is based on Execution State. Execution State includes time, Achievement Threshold, Variance Threshold. Achievement Threshold can include any specific measured value. Variance Threshold is an Achievement Threshold that is specifically based on a relative change in the measured value.

In an embodiment, Sequences are composited with overlay patterns. These overlay patterns include tool patterns and known Subject Patterns. Subject Patterns include motion associated with respiration.

In an embodiment, Protocol Selection includes Region Specifications that generates a stroke list. Region Specifications include targets, Body Regions to apply more attention, Body Regions to apply less attention, and Body Regions to avoid.

Strokes can be naturally generated by therapists and trained as recordings of their manipulation of a Subject. The manipulation can include direct manipulation of a robotic end effector, manipulation of a tracked object, and analysis of visually sensed manipulation (e.g. video and depth data).

In an embodiment, the Motion Tracking System utilized to train massages is based on an Infrared (IR), Inertial Measurement Unit (IMU) Motion Tracking System. In an embodiment, the Motion Tracking System can be an HTC Vive, Optitrack, Vicon, or similar Motion Tracking System. In a further embodiment, the Motion Tracking System is attached to a Touchpoint that is moved along the Subject's Body while performing a massage to be recorded. In an embodiment, any three dimensional (3D) position and orientation sensor can be utilized, including the Hexagonmi portable measuring arm.

In an embodiment, the Motion Tracking System has an Online Validation Procedure that continually monitors the training to indicate warnings and errors as Exception Events for the operator or Therapist performing the training/teaching. The Online Validation Procedure includes Exception Events that indicate the predicted reachability and manipulability, during playback, of the robot for the given position of the manipulators. In a further embodiment, the Exception Events include incursion information for parts of the body that are important to avoid. Examples of areas to avoid include the spine, the skull, and any regions that would be considered inappropriate.

In an embodiment, the Massage Protocol implementation has a high level plan with blocks that group strokes. At this level, avoidance zones are handled through steering and skipping. Steering generates strokes that move around the avoidance area by selecting alternative blocks that don't include the area to avoid. Skipping allows for low force motion through the Block's intended path. In an embodiment, steering generates motion going around the avoidance area rather than utilizing a previously saved motion.

In an embodiment, the dimensions and articulation of the individual Body are estimated with a Body Model. The Body Model incorporates shape parameters that generate a set of spatial points defining the Body shape in a neutral position. The Body Model incorporates pose parameters that articulate the parts of the Body in a manner similar to how a Body articulates based on skeletal joints. The Shape model also models the shape morphological changes associated with the articulation of the joints. The Body Model also has parameters for the shape variation associated with the contraction and relaxation of the skeletal muscles. The Body Model's Shape, Articulation, and Articulation Shape are combined to generate a continuous Body Surface for the Body. The Body Surface is a Body Mesh comprising Surface Vertices and Surface Facets. The Surface Vertices are uniquely indexed with a unique Vertex Index. Vertex Indices from Body Models with different parameterizations correspond to the same Anatomical Position for each separate Body Model.

Figure 6:
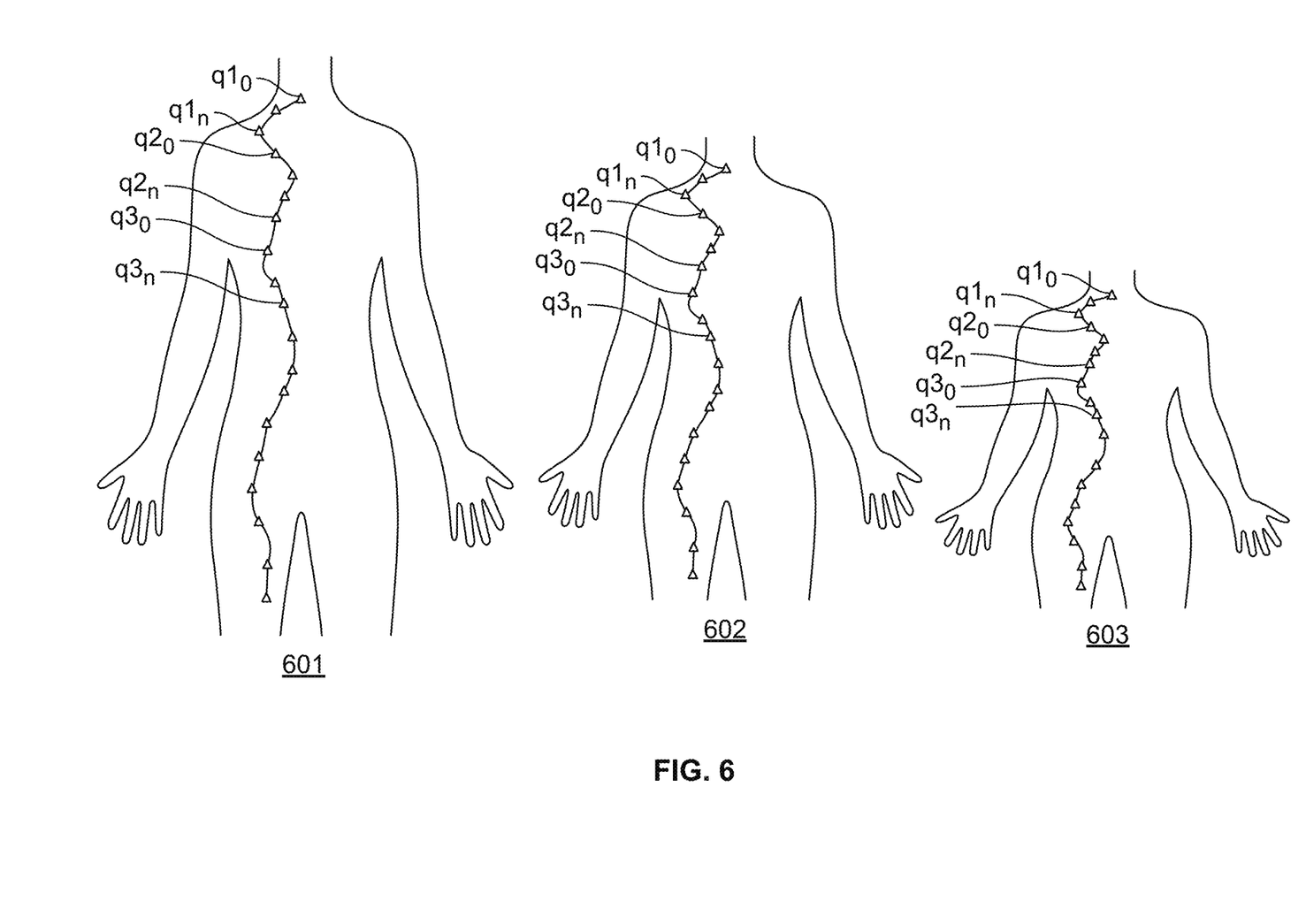
FIG. 6 shows an embodiment of a mapping of trajectories according to the present invention.

In an embodiment, a Procedure for Trajectory Retargeting includes one or more of the following steps:
1. Fit the Source Subject Body Model to the sensed data
2. Record massage pose and sensed force in Cartesian space
3. Generate the Source Encoding as pose and sensed force relative to the Source Subject Body Model
4. Generate the Canonical Encoding by transforming the Source Encoding to the canonical body model
5. Fit the Target Subject Body Model to the sensed data
6. Generate the Target Encoding by transforming the Canonical Encoding to Target Body Model
7. Decode Target Encoding into Cartesian coordinates FIG. 6 depicts an embodiment of mapping of trajectories in the Trajectory Retargeting Process. Shown in this figure are the Source Body Model (601), the Canonical Body Model (602), and the Target Body Model (603). The detail views of the Subjects (601, 602, 603) depict a Massage Plan on the left side of the back of the body, composed of Massage Strokes (q1, q2, q3). Between each Stroke is a short connection motion indicated as a dashed line which is automatically generated at runtime. Each Massage Stroke is composed of Massage Goals (e.g. $q1.sub.0$ through $q1.sub.n$).

In an embodiment, the Trajectory Retargeting Process fits the Source Subject Body Model (601) to the sensed data. Then the massage is recorded as pose and sensed force in Cartesian space. Then, the Source Encoding is generated as pose and sensed force relative to the Source Subject Body Model. Then, Canonical Encoding is generated by transforming the Source Encoding to the Canonical Body Model (602). Then, the Target Subject Body Model (603) is fit to the sensed data. Then, the Target Encoding is generated by transforming the Canonical Encoding to Target Body Model. Then, Target Encoding is decoded into Cartesian coordinates. These Cartesian coordinates are then used to control the robot to perform the massage strokes.

In an embodiment, an Anatomical Model is estimated based on the Body Model's Anatomical Positions indicated by the Body Model's Vertex Indices. The Anatomical Model is fit to the Body Model's Shape. The Anatomical Model's Anatomical Articulation is estimated using the Body Model's Body Articulation. and the underlying Body Model Articulated Shape is used to estimate the Anatomical Model's Articulated Shape. The Anatomical Model includes estimations for the internal soft and hard Tissue Structures. The Tissue Structures estimate the morphology of the underlying tissue based on the gross scale and proportions of the Anatomical Model. Tissue Structures include the Musculoskeletal tissue, Adipose tissue, and Major Internal Organs.

In an embodiment, the Tissue State Model utilized the Body Model and the Anatomical Model to estimate the position and physical characteristics of Palpation Targets.

In an embodiment, the output from the Palpation System is used by the Massage Generation system, primarily in the following ways. Firstly, overall muscle stiffness is used as a feedback mechanism in the Monitor State to determine during execution if a selected stroke should have its duration increased or decreased to achieve a desired outcome.

In an embodiment, when a desired outcome is defined as reducing tissue stiffness through the application of a selected stroke. When a desired stiffness reduction threshold is supplied, the Palpation System can assess the stiffness at the start of the stroke and then monitor it throughout the application of that stroke. If after completion of the indicated stroke, the tissue stiffness has not been reduced by the desired amount, the stroke can be repeated, or a new stroke can be selected, or in the case of artificially generated strokes, the stroke can be extended.

Secondly, in an embodiment of Trigger Point treatment, the Palpation System is used to detect the presence of Adhesions and Trigger Points along with their locations on the body. The location of these treatment points is then used to calculate a new treatment stroke, which is applied to the problem area. Once treatment is complete, the Palpation System can again be used to confirm that any problem areas have been properly treated.

In an embodiment, processing of the therapeutic tissue techniques is achieved by defining a model based on a corpus of recorded strokes. The associations between the strokes are learned through a machine learning technique. A neural network is trained to detect synonymous strokes when given a sequence of strokes and suggests the next stroke. Each stroke is represented as a feature vector such that the strokes can be compared using normalized cross correlation. The similarity metric is based on the semantic similarity between the strokes as assessed by therapeutic experts.

In an embodiment, the feature space is achieved through modeling the temporal structure of the strokes using an Embedding Model. Sensor data is iteratively segmented using the mapping from the embedded space, resulting in a Stroke Segmentation. Strokes that are similar in the embedding space are used to segment a new stroke into substrokes and assign candidate metadata to the new stroke.

In an embodiment, the Embedding Model, equivalently the Embedding Encoding, is achieved by training an Autoencoder Deep Learning model. In a further embodiment, the Autoencoder is a Variational Autoencoder.

In an embodiment, the Stroke Segmentation results in Stroke Segments that initially are associated by a Sequential Relationship, specifically one based on their temporal order. In a further embodiment, the Sequential Relationship is based on regional dependencies that restrict the stroke sequences based on starting and ending positions relative to the body regions.

In an embodiment, the Sequential Relationship is represented by the order of the body regions. In a further embodiment, the Sequential Relationship is represented by the order of the muscles that the strokes manipulate. In a further embodiment, the Sequential Relationship is represented by the path and stroke dynamics of the Massage Goals.

In an embodiment, strokes are broken into smaller Stroke Motion segments that include not only a series of Massage Goals but also other Stroke Motion Context information that can include the characteristics of the surface being manipulated, the style of the stroke, and the underlying tissue constituency.

In an embodiment, the Stroke Motion segments are used to train an Autoencoder, the Stroke Motion Matching Model, resulting in a feature space where the current Stroke Motion segment sequence has an extrapolated Stroke Motion Step. The Stroke Motion Step provides an embedded vector for a possible next Stroke Segment that is then synthesized by using the Decoder part of the Autoendoder to generate the predicted Stroke Motion.

In an embodiment, the Stroke Motion Matching Model selects steps based on changes in the Surface being manipulated, the Style of massage changing, the difference in the constituency of the tissue underlying the Surface that is in contact.

In an embodiment, the contact path on the Surface is represented as a texture map. The contact path represented on the 2D surface is used to project the path onto the 3D model in order to avoid discontinuities in the 3D model.

In an embodiment, the Massage Goals are converted to Contact Goals. The Contact Goals are derived from the surface area contact between the Touchpoint and the Surface of the Subject's Body, namely the Contact Patch. The Contact Goal is further defined by a Pressure Goal derived from the pressure resulting from the application of the Force Goal distributed across the Contact Patch.

In an embodiment, a Pressure Control is defined to allow the commanded pose, orientation, and force goals commanded to the robot to be formulated based on achieving the Contact Goals, irrespective of the actual pose, orientation, and force used when recording the massage. In a further embodiment, the Pressure Control can be used as an additional degree of freedom for the robot's configuration space. In a further embodiment, the Pressure Control can be used as an additional degree of freedom to accommodate situations in which Subject Bodies present drastically differing orientations for contact.

In an embodiment, the Pressure Control is used to configure the robot and the point of contact for the Touchpoint are determined to achieve any Operational Goal including preservation of commanded torque, limiting joint velocity and acceleration, avoiding robot arm incursion to the region proximal to the Subject's Body.

In an embodiment, the Contact Patch is determined through FEA modeling of the deformation of the Touchpoint and the Body's Surface when in contact. In a further embodiment, an estimate of the FEA predicted deformation is approximated using Thin Plate Splines applied to the meshes of the two models.

In an embodiment, the Body Fitting Procedure has two inputs specified, the first is a color image and the other is a depth image. These inputs are combined into a single feature vector that is used to train a Machine Learning model. In a further embodiment, the Machine Learning model is a Deep Learning model, specifically a Semantic Segmentation model. In a further embodiment, the Semantic Segmentation model is any one of the following: a FCN, a U-Net, MobileNetv3.

In an embodiment, the Contact Patch Generation process utilizes a Contact Patch Model. In an embodiment, the Model is a Gaussian Mixture Model. The Model defines a Contact Surface and the distribution of pressure across the surface is a function of the GMM's constituent Radial Basis Functions (RBFs). In a further embodiment, the surface pressure is transformed to underlying tissue layers through a Tissue Transform Projection process. In an embodiment, this process is a direct translation of the surface to the underlying tissue through a translation of the surface vertices in the opposite direction indicated by the surface normals or the single resultant surface normal for the whole patch.

In an embodiment, the Trajectory Retargeting is a process for converting recorded robot goals from Cartesian space to a Body Parameterization. In a further embodiment, the Body Parameterization uses the Barycentric Coordinate system, which represents the position of trajectory points relative to a triangle in a given mesh, specifically the mesh of the Body Model. A Body Model, represented as a deformable 3D mesh, is parameterized to fit multiple Subjects while maintaining the coherency of the relative surface areas of their bodies, and correspondingly the specific regions of their bodies. The Body Parameterization maps encoded Cartesian positions from one deformation of the Body Model to another. Trajectory Retargeting is achieved by the mapping of positions in Body Parameters, between the two realizations of the body model meshes, converting these positions to Cartesian coordinates for generating goals for the robot.

In an embodiment, the Trajectory Retargeting is achieved through encoding the positions using the Body Model's vertex identifiers. These identifiers are used to map Cartesian positions onto the Body Model by finding the mesh faces closest to a given point, and then expanding this subset of the mesh along the vertex normals until the mesh intersects with the point in question. The identified face and the point's intersecting position are used to retarget the point from one Subject to another.

In an embodiment, the Trajectory Retargeting is processed in a Body Texture Map. The Body Texture Map is similar to 2D texture maps utilized in application of textures to 3D models, sometimes referred to as a UV map. In the case where the Trajectory positions in the Body Model's Barycentric representation of the Body Parameters are not continuous and traversal of the topology of the vertices requires complex techniques to resolve topological, the Body Texture Map offers a continuous surface that can be mapped back to Barycentric coordinates relative to the Body Model, and subsequently Cartesian coordinates for commanding desired robot positions. This allows the Trajectory Retargeting system to resolve these ambiguities without having to resort to more complex techniques, including analysis of principal curvature of the Body Model.

In an embodiment, the determination of symmetries in the Body Texture Map enable the mirroring of coordinates to facilitate the application of a massage intended for one half of the Subject's body to be applied to the other half of the Subject's body.

In an embodiment, the Body Texture Map is utilized to generate Massage Goals based on diagrams mapped to the Body Texture Map. In a further embodiment, the diagram mapped to the Body Texture Map is a Trigger Point Map.

In an embodiment, the Body Texture Map is utilized to map the Contact Patch from one body to another, thereby retargeting any goals associated with the contact patch.

In another embodiment, the mapping of Cartesian goals to and from It is also possible to find a path on the Body Texture Map between two Body Texture Map coordinates. Body Texture Map coordinates are mapped back into Barycentric coordinates. Construction of specific Body Texture Maps is utilized to achieve additional Operational Goals. For example, for the purpose of massage this technique is used to calculate Barycentric coordinates that are mirrored across the Body Model vertices associated with the Spine. In another embodiment, a mirror plane is drawn on a single limb of the Body Model providing mirroring to either side of the limb.

In an embodiment, two or more robotic arms are utilized to provide Coordinated Manipulation of the Subject's Body. The Coordinated Manipulation includes any complimentary coordination of motion, application of forces, combined with Sensed Feedback from the force/torque sensors in each arm.

Embodiments detailing the utilization of Coordinated Manipulation describe the use of two manipulators, specifically two robotic arms and the coordination of their respective TouchPoints. The description of two manipulators is not limited to only two manipulators, and when described, each manipulator can be one or more manipulators.

In an embodiment, the Coordinated Manipulation includes using one manipulator to divert the Subject's attention in order to minimize the Subject tensing muscles in contact with the other manipulator.

In an embodiment, the Coordinated Manipulation utilizes one manipulator to brush the surface of the Subject's Body or lightly pat the surface in order to cue the Subject's reflexive recovery from an intense sequence of strokes.

In an embodiment, the Coordinated Manipulation includes using one manipulator leaving contact with one Region of the Subject's Body to join another manipulator already in contact with another Region of the Subject's Body.

In an embodiment, the Coordinated Manipulation includes Control Law, a Coordinated Control Law, definitions that adjust the pressure of one manipulator based on sensing the pressure from another manipulator, as sensed through the Subject's Body.

In an embodiment, the Coordinated Control Law includes using one manipulator to dampen mechanical oscilitory disturbances in the Subject's Body being induced by another manipulator.

Features of the various embodiments of the above-identified system and method described herein can be modeled and/or effected and/or controlled by a general computer, special purpose computer, a processor, and a smart device having a processor. The various embodiments described herein, and those equivalents thereto, can be used for a variety of nonanalogous objects, e.g., human body, animal body, soft body having deformable characteristics, a non-homogenous body having soft and hard features. The various embodiments described herein, and those equivalents thereto, can be used for massage applications, sensing applications, modeling applications, and others.

The modifications listed herein and other modifications can be made by those in the art without departing from the ambit of the invention. Although the invention has been described above with reference to specific embodiments, the invention is not limited to the above embodiments and the specific configurations shown in the drawings. For example, some components shown can be combined with each other as one embodiment, and/or a component can be divided into several subcomponents, and/or any other known or available component can be added. The processes are not limited to those shown in the examples. Those skilled in the art will appreciate that the invention can be implemented in other ways without departing from the substantive features of the invention. For example, features and embodiments described above can be combined with and without each other. The present embodiments are therefore to be considered in all respects as illustrative and not restrictive. Other embodiments can be utilized and derived therefrom, such that structural and logical substitutions and changes can be made without departing from the scope of this disclosure. This Specification, therefore, is not to be taken in a limiting sense, along with the full range of equivalents to which such claims are entitled.

Such embodiments of the inventive subject matter can be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose can be substituted for the specific embodiments shown. This disclosure is intended to cover any and all adaptations and/or variations of various embodiments. Combinations of the above embodiments, and other embodiments not specifically described herein, will be apparent to those of ordinary skill in the art upon reviewing the above description.

What is claimed is:

1. A method, comprising:
   recording, via at least one processor and during a capture period, first data associated with a first sequence of motions of an end effector of a robotic manipulator while the end effector is in contact with a reference body, to produce recorded data including tool data, force data, and contact location data;
   generating, via the at least one processor, a motion plan based on the recorded data, the motion plan specifying a second sequence of motions different from the first sequence of motions; and
   causing the robotic manipulator to execute the motion plan in a presence of a deformable body, during a playback period subsequent to the capture period, and while the end effector is in contact with the deformable body.

2. The method of claim 1, further comprising generating, via the at least one processor, a motion template based on the recorded first data after the capture period and before the playback period, the generating the motion plan being based on the motion template and a body model associated with the deformable body.

3. The method of claim 1, wherein the generating the motion plan includes combining a plurality of massage goals into a sequence.

4. The method of claim 3, wherein the combining the plurality of massage goals into the sequence includes interpolating artificially generated massage goals among the plurality of massage goals, to produce smooth motion at each transition from a plurality of transitions of the sequence.

5. The method of claim 4, wherein the interpolating includes at least one of linear interpolation, spherical linear interpolation, interpolation in Cartesian space, or polynomial interpolation.

6. The method of claim 4, wherein the interpolating includes one of piecewise linear interpolation or piecewise polynomial interpolation.

7. The method of claim 1, further comprising generating a body model of the deformable body, the generating the motion plan further based on the body model.

8. The method of claim 7, wherein the motion plan includes a sequence of massage goals, the generating the motion plan including at least one of removing a massage goal from the sequence of massage goals, adding a new massage goal to the sequence of massage goals, or altering a massage goal from the sequence of massage goals, in response to detecting that at least one path of the sequence of massage goals is not topologically valid.

9. The method of claim 7, wherein the body model includes a deformable three-dimensional (3D) mesh.

10. The method of claim 7, wherein generating the body model includes determining at least one of a body shape, a pose, or a position of the deformable body based on imagery from at least one camera.

11. The method of claim 10, wherein the at least one camera includes a depth sensing camera.

12. The method of claim 1, further comprising:
    detecting, via the processor and during the execution of the motion plan, that at least one of a change in a motion of the deformable body, a change in an articulation of the deformable body, or a change in a shape of the deformable body exceeds a predefined threshold value; and
    in response to detecting that the at least one of the change in the motion of the deformable body, the change in the articulation of the deformable body, or the change in the shape of the deformable body exceeds the predefined threshold value, modifying the motion plan during execution of the motion plan.

13. The method of claim 12, wherein the motion plan includes a sequence of massage goals, and the modifying the motion plan includes at least one of: removing a massage goal from the sequence of massage goals, adding a new massage goal to the sequence of massage goals, or altering a massage goal from the sequence of massage goals.

14. The method of claim 1, wherein the generating the motion plan includes combining a plurality of motion paths into a sequence.

15. The method of claim 1, wherein the generating the motion plan includes at least one of ordering, blending, or layering geometric primitives from a plurality of geometric primitives.

16. The method of claim 1, wherein the deformable body is a human user, the method further comprising modifying the motion plan during execution of the motion plan in response to a user input received at the processor one of during or before execution of the motion plan, the user input resulting from an interaction of the human user with a user interface operably coupled to the processor.

17. The method of claim 16, wherein the generating the motion plan is further based on a body model of the deformable body, and includes scaling at least one force goal from a plurality of force goals and arranging the plurality of force goals in a sequence.

18. The method of claim 1, wherein the generating the motion plan is further based on a dynamic tool parameter.

19. The method of claim 1, wherein the generating the motion plan is further based on a desired therapeutic effect.

20. The method of claim 1, wherein each motion from the second sequence of motions includes a massage stroke.

* * * * *